(12) United States Patent
Weiss et al.

(10) Patent No.: US 8,084,226 B2
(45) Date of Patent: Dec. 27, 2011

(54) METHOD FOR SITE-SPECIFIC PROTEIN MODIFICATIONS

(75) Inventors: Shimon Weiss, Los Angeles, CA (US); Marcus Jäger, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 321 days.

(21) Appl. No.: 11/490,240

(22) Filed: Jul. 21, 2006

(65) Prior Publication Data

US 2007/0020690 A1   Jan. 25, 2007

Related U.S. Application Data

(60) Provisional application No. 60/701,293, filed on Jul. 21, 2005.

(51) Int. Cl.
*C12P 1/00* (2006.01)
*A61K 38/00* (2006.01)
(52) U.S. Cl. .......................................... 435/41; 530/345
(58) Field of Classification Search .................. None
See application file for complete search history.

(56) References Cited

OTHER PUBLICATIONS

Jager et al., Protein-protein interactions as a tool for site-specific labeling proteins, Protein Science, published online: Jun. 29, 2005, 14: 2059-2068.*
Ngo et al., in The Protein Folding Problem and Tertiary Structure Prediction, 1994, Merz et al. (ed.), Birkhauser, Boston, MA, pp. 433 and 492-495.*
Onuchic, J. N.; Luthey-Schulten, Z.; Wolynes, P. G. *Ann. Rev. Phys. Chem.* 1997, 48, 545-600.
Dill, K. A.; Chan, H. S. *Nat. Struct. Biol.* 1997, 4, 10-19.
Shea, J. E.; Brooks 3rd, C. L. *Ann. Rev. Phys. Chem.* 2001, 52, 499-535.
Talaga, D. S.; Lau, W. L.; Roder, H.; Tang, J.; Jia, Y.; DeGrado, W. F.; Hochstrasser, R. M. *Proc. Natl. Acad. Sci USA* 2000, 97, 13021-13026.
Deniz, A. A.; Laurence, T. A.; Beligere, G. S.; Dahan, M.; Martin, A. B.; Chemla, D. S.; Dawson, P. E.; Schultz, P. G.; Weiss, S. *Proc. Natl. Acad. Sci USA* 2000, 97, 5197-5184.
Schuler, B.; Lipman, E. A.; Eaton, W. A. *Nature* 2002, 419, 743-747.
Rhoades, E.; Gussakovsky, E.; Haran, G. *Proc. Natl. Acad. Sci USA* 2003, 100, 3197-3202.
Rhoades, E.; Cohen, M.; Schuler, B.; Haran, G. *J. Am. Chem. Soc.* 2004.
Lipman, E. A.; Schuler, B.; Bakajin, O.; Eaton, W. A. *Science* 2003, 301, 1233-1235.
Weiss, S. *Nat. Struct. Biol.* 2000, 7, 724-729.
Selvin, P. R. *Nat. Struct. Biol.* 2000, 7, 730-734.
Deniz, A. A.; Laurence, T. A.; Dahan, M.; Chemla, D. S.; Schultz, P. G.; Weiss, S. *Annu. Rev. Phys. Chem.* 2001, 52, 233-253.
Ha, T. *Methods* 2001, 25, 78-86.
Ha, T. *Biochemistry* 2004, 43, 4055-4063.
Clegg, R. M. *Methods Enzymol.* 1992, 211, 353-388.
Stryer, L.; Haugland, R. P. *Proc. Natl. Acad. Sci. USA* 1967, 58, 719-726.
Jia, Y.; Talaga, D. S.; Lau, W. L.; Lu, H. S. M.; DeGrado, W. F.; Hochstrasser, R. M. *Chem. Phys.* 1999, 247, 69-83.
Hohng, S.; Joo, C.; Ha, T. *Biophys. J.* 2004, 87, 1328-1337.
Liu, J.; Lu, Y. *J. Am. Chem. Soc.* 2002, 124, 15208-15216.
Watrob, H. M.; Pan, C.; Barkley, M. D. *J. Am. Chem. Soc.* 2003, 125, 7336-7343.
Sinev, M.; Landsmann, P.; Sineva, E.; Ittah, V.; Haas, E. *Bioconjugate Chem.* 2000, 11, 352-362.
Ratner, V.; Kahana, E.; Eichler, M.; Haas, E. *Bioconjugate Chem.* 2002, 13, 1163-1170.
Moerner, W. E.; Orrit, M. *Science* 1999, 283, 1670-1676.
Brasselet, S.; Moerner, W. E. *Single Molecules* 2000, 1, 17-23.
Dawson, P. E.; Muir, T. W.; Clark-Lewis, I.; Kent, S. B. *Science* 1994, 266, 776-779.
Muir, T. W.; Sondhi, D.; Cole, P. A. *Proc. Natl. Acad. Sci. USA* 1998, 95, 6705-6710.
Tolbert, T. J.; Wong, C. H. *Angew. Chem. Int. Ed.* 2002, 41, 2171-2174.
Schuler, B.; Pannell, L. K. *Bioconjugate Chem.* 2002, 13, 1039-1043.
Geoghegan, K. F.; Stroh, J. G. *Bioconjugate Chem.* 1992, 3, 138-146.
Shao, J.; Tam, J. P. *J. Am. Chem. Soc.* 1995, 117, 3893-3898.
Zhang, L.; Tam, J. P. *Anal. Biochem.* 1996, 233, 87-93.
Guillaumie, F.; Thomas, O. R. T.; Jensen, K. J. *Bioconjugate Chem.* 2002, 13, 285-294.
Chelius, D.; Shaler, T. A. *Bioconjugate Chem.* 2003, 14, 205-211.
Chin, J. W.; Santoro, S. W.; Martin, A. B.; King, D. S.; Wang, L.; Schultz, P. G. *J. Am. Chem. Soc.* 2002, 124, 9026-9027.
Deiters, A.; Cropp, T. A.; Mukherji, M.; Chin, J. W.; Anderson, J. C.; Schultz, P. G. *J. Am. Chem. Soc.* 2003, 125, 11782-11783.
Wang, L.; Zhang, Z.; Brock, A.; Schultz, P. G. *Proc. Natl. Acad. Sci USA* 2002, 100, 56-61.
Zhang, Z.; Smith, B. A. C.; Wang, L.; Brock, A.; Cho, C.; Schultz, P. G. *Biochemistry* 2003.
Janin, J. *Proteins* 1997, 28, 153-161.
Lo Conte, L.; Chothia, C.; Janin, J. *J. Mol. Biol.* 1999, 285, 2177-2198.
Jones, S.; Marin, A.; Thornton, J. M. *Protein Eng.* 2000, 13, 77-82.
Chakrabarti, P.; Janin, J. *Proteins* 2002, 47, 334-343.
Radisky, E. S.; Koshland Jr., D. E. *Proc. Natl. Acad. Sci USA* 2002, 99, 10316-10321.
Radisky, E. S.; Koshland Jr., D. E. *Biochemistry* 2003, 42, 6484-6492.
Bryan, P.; Wang, I.; Hoskins, J.; Ruvinov, S.; Strausberg, S.; Alexander, P.; Almog, O.; Gilliland, G.; Gallagher, T. *Biochemistry* 1995, 34, 10310-10318.

(Continued)

*Primary Examiner* — Suzanne M Noakes
*Assistant Examiner* — Jae W Lee
(74) *Attorney, Agent, or Firm* — Venable LLP; Nancy J. Axelrod; Henry J. Daley (57) ABSTRACT

A method for site-specific modification of protein molecules includes providing a protein molecule having at least first and second non-terminal Cys residues at respective first and second sites within the protein molecule, providing a blocking molecule that is suitable to interact with the protein molecule to selectively block the second non-terminal Cys residue to prevent modifications of the second non-terminal Cys residue while leaving the first non-terminal Cys residue unblocked, and providing a Cys-modifying molecule that is suitable to modify the first non-terminal Cys residue. The blocking molecule according to an embodiment of the invention may be a protein molecule, DNA, an aptamer or synthetic organic molecules. The Cys-modifying molecule according to an embodiment of the invention may be a fluorophore, biotin, spin label, a sugar or a non-natural amino acid analogue.

21 Claims, 3 Drawing Sheets

OTHER PUBLICATIONS

Pace, C. N. *Methods Enzymol.* 1986, 131, 266-280.
Santoro, M. M.; Bolen, D. W. *Biochemistry* 1988, 27, 8063-8068.
Myers, J. K.; Pace, C. N.; Scholtz, J. M. *Protein Sci.* 1995, 4, 2138-2148.
Kapanidis, A. N.; Lee, N. K.; Laurence, T. A.; Doose, S.; Margeat, E.; Weiss, S. *Proc. Natl. Acad. Sci USA* 2004, 101, 8936-8941.
Dahan, M.; Deniz, A. A.; Ha, T.; Chemla, D. S.; Schultz, P. G.; Weiss, S. *Chem. Phys.* 1999, 247, 85-106.
Bogan, A. A.; Thorn, K. S. *J. Mol. Biol.* 1998, 280, 1-9.
Jackson, S. E.; Fersht, A. R. *Biochemistry* 1991, 30, 10428-10435.
Jackson, S. E.; Fersht, A. R. *Biochemistry* 1994, 33, 13880-13887.
Radisky, E. S.; Kwan, G.; Lu, K.; Koshland Jr., D. E. *Biochemistry* 2004, 43, 13648-13656.
Eftink, M. *Methods Enzymol.* 1997, 278, 221-257.
Deniz, A. A.; Dahan, M.; Grunwell, J. R.; Ha, T.; Faulhaber, A. E.; Chemla, D. S.; Weiss, S.; Schultz, P. G. *Proc. Natl. Acad. Sci. USA* 1999, 96, 3670-3675.
Buckle, A. M.; Schreiber, G.; Fersht, A. R. *Biochemistry* 1994, 33, 8878-8889.
Welch, M.; Chinardet, N.; Mourey, L.; Birck, C.; Samama, J. P. *Nat. Struct. Biol.* 1998, 5, 25-29.
Lim, D.; Park, H. U.; De Castro, L.; Kang, S. G.; Lee, H. S.; Jensen, S.; Lee, K. L.; Strynadka, N. C. J. *Nat. Struct. Biol.* 2001, 8, 848-852.
Fieulaine, S.; Morera, S.; Poncet, S.; Mijakovic, I.; Galinier, A.; Janin, J.; Deutscher, J.; Nessler, S. *Proc. Natl. Acad. Sci USA* 2002, 99, 13437-13441.
Kelley, R. F.; O'Connell, M. P. *Biochemistry* 1993, 32, 6828-6835.
Hawkins, R. E.; Russell, S. J.; Baier, M.; Winter, G. *J. Mol. Biol.* 1993, 234, 958-964.
Li, H.; Dunn, J. J.; Luft, B. J.; Lawson, C. L. *Proc. Natl. Acad. Sci USA* 1997, 94, 3584-3589.
Ding, W.; Huang, X.; Yang, X.; Dunn, J. J.; Luft, B. J.; Koide, S.; Lawson, C. L. *J. Mol. Biol.* 2000, 302, 1153-1164.
Mandell, J. G.; Falick, A. M.; Komives, E. A. *Proc. Natl. Acad. Sci USA* 1998, 95, 14705-14710.
Hughes, C. A.; Mandell, J. G.; Anand, G. S.; Stock, A. M.; Komives, E. A. *J. Mol. Biol.* 2001, 307, 967-976.
Anand, G. S.; Law, D.; Mandell, J. G.; Snead, A. S.; Tsigelny, I.; Taylor, S. S.; Ten Eyck, L. F.; Komives, E. A. *Proc. Natl. Acad. Sci. USA* 2003, 100, 13264-13269.
Chu, F.; Shan, S.; Moustakas, D. T.; Alber, F.; Egea, P. F.; Stroud, R. M.; Walter, P.; Burlingame, A. A. *Proc. Natl. Acad. Sci USA* 2004, 101, 16454-16459.
Feldhaus, M. J.; Siegel, R. W.; Opresko, L. K.; Coleman, J. R.; Feldhaus, J. M.; Yeung, Y. A.; Cochran, J. R.; Heinzelman, P.; Colby, D.; Swers, J.; Graff, C.; Wiley, H. S.; Wittrup, K. D. *Nat. Biotechnol.* 2003, 21, 163-170.

\* cited by examiner

METHOD FOR SITE-SPECIFIC PROTEIN MODIFICATIONS

This invention was made with Government support under Grant No. GM065382, awarded by the National Institutes of Health. The Government has certain rights in this invention.

CROSS-REFERENCE TO RELATED APPLICATION

This application claims priority to U.S. Application Ser. No. 60/701,293 filed Jul. 21, 2006, the entire contents of which are hereby incorporated by reference.

BACKGROUND

1. Field of Invention

This application relates to a method for making site-specific protein modifications, and more particularly to modifications of protein molecules having at least two non-terminal cysteine residues; and to products comprising protein molecules so modified.

2. Discussion of Related Art

The contents of all references, including articles, published patent applications and patents referred to anywhere in this specification are hereby incorporated by reference.

Biochemical processes often exhibit a large degree of heterogeneity. A prominent example is the myriad of successive conformations experienced by an unfolded (denatured) protein along its folding trajectory towards its native state.[1-3] Classical ensemble methods yield only mean values, averaged over large ensembles of molecules. Single molecule experiments, on the other hand, allow the examination of each molecule individually. Meaningful information about the microscopic distribution of conformations, trajectories and sequences of events can be obtained that are hidden on ensemble level.[4-9]

Fluorescence resonance energy transfer (FRET) between a single donor (D) fluorophore and a complementary single acceptor (A) fluorophore (single-pair FRET, or spFRET) is a particularly powerful and sensitive method for monitoring protein folding reactions at single molecule resolution.[10-14] The FRET-efficiency E is a sensitive function of the D/A-distance R, as $E=[1+(R/R_0)^6]^{-1}$. $R_0$ is a constant that corresponds to a D/A-distance at which E=50%.[15] Because of its dependence on the distance R, spFRET can be used as a distance ruler to track intrachain-conformational dynamics in polypeptide chains in the 2 to 8 nm range.[16]

A critical component in a single molecule spFRET protein folding experiment is the ability to label a polypeptide chain with a unique D/A-pair in a controlled and site-specific way. In the past, single molecule spFRET folding studies have been performed with chemically synthesized polypeptides.[4,5,17] Chemical synthesis of polypeptides has the advantage that side chain protecting groups can be exploited to facilitate site-specific two-color labeling, but its extension to 3-color labeling[18-20] or the labeling of proteins of more than 100 amino acids in length are difficult to achieve.

Recombinant expression of proteins offers more flexibility with respect to chain size. Cysteine (Cys) residues are statistically underrepresented in protein sequences, and many proteins are either devoid of Cys or intrinsic Cys can be removed by site-directed mutagenesis. A unique pair of Cys can then be (re)introduced into the protein at carefully selected surface accessible positions for conjugation with thiol-specific maleimide-functionalized fluorophores. For stoichiometric labeling of double-Cys proteins with a D/A-pair, a two step protocol is usually employed.[6,7,21,22] First, the protein is reacted with a single fluorophore, added at stoichiometric ratio to minimize double labeling. Singly modified protein molecules are then separated chromatographically from unreacted or doubly-labeled molecules and reacted with the second, complementary, dye. Unfortunately, this two-step sequential labeling is not strictly site-specific. Unless the dye-accessibility of the two thiol-groups differ drastically, the first added fluorophore can be attached to either of the two sulfhydryl groups, giving rise to mixtures of D/A-labeled molecules and the dye-permutated, A/D-analogues.[22] Such mixtures can lead to unwanted sample heterogeneity, as the conjugated dyes can exert a positional-dependent perturbation of the folding free energy of the modified protein. Also, heterogeneities in photophysical properties of the fluorophores due to different local environments (local charge, pH, or hydrophobicity) could complicate the interpretation of spFRET measurements.[23,23] Lastly, strict site-specificity of labeling is absolutely mandatory for more sophisticated three- or multi-color FRET experiments.[18-20]

To increase the site-specificity of sequential labeling, labeling chemistries have been developed that selectively modify N-terminal Cys residues. For example, N-terminal Cys specifically react with thioester-moieties into a stable amide bond.[25-27] This chemistry has been exploited by Schuler and Pannell[28] to label a short synthetic model peptide at the N-terminus using a commercial fluorophore chemically modified with a thiobenzylester functionality. Other strategies involve the oxidation of an N-terminal serine (Ser) or threonine (Thr) to the corresponding aldehyde and subsequent coupling with fluorophore containing hydrazine, alkoxyamine or hydrazide functionalities,[29] or the specific reaction of an N-terminal Cys with aldehydes into thiazolidines, a reaction that has been utilized to label and immobilize peptides and proteins.[30-33]

Recently, Schultz and colleagues reported a novel strategy for site-specific incorporation of non-natural amino acids into proteins in vivo in response to the amber stop codon using genetically modified orthogonal t-RNA/t-RNA synthetase pairs with altered amino acid specificities. Incorporation of non-natural amino acids with keto or azide functionalities into soluble cytoplasmic as well as membrane proteins have been achieved, with excellent yields and high fidelity.[34-37] The unique chemistry of the keto and azide groups can be used for site-specific dye-conjugation either directly in vivo (e.g. by addition of a hydrazine-functionalized dye to the growth medium to label the non-natural keto-group) or in vitro using purified protein samples. Although very powerful, this technique is not yet broadly available to the scientific community. There thus remains a need for at least improved techniques for site-specific labeling of proteins.

SUMMARY

Further objects and advantages will become apparent from a consideration of the description, drawings and examples.

A method for site-specific protein labeling according to an embodiment of this invention includes providing a first protein molecule having at least first and second non-terminal Cys residues at respective first and second sites within the first protein molecule, providing a second protein molecule that is suitable to interact with the first protein molecule to selectively block the second non-terminal Cys residue from fluorophore binding while leaving the first non-terminal Cys residue unblocked, and providing a fluorophore that is suitable to bind to the first non-terminal Cys residue. The first protein molecule can be a recombinant protein molecule in which at least one of the at least first and second non-terminal Cys residues is introduced or re-introduced at a selected site within the first protein. The method for site-specific protein labeling can also include separating the second protein molecule from the first protein molecule after the second protein molecule interacts with the first protein molecule and after the fluorophore binds to the first non-terminal Cys residue, after which the method for site-specific protein labeling may further include providing a second fluorophore that is suitable to bind to the second non-terminal Cys residue.

The first-mentioned fluorophore can be a donor fluorophore and the second fluorophore can be an acceptor fluorophore sui table to provide a donor-acceptor pair for fluorescence resonance energy transfer measurements. The first protein molecule can have more than two Cys residues at the respective first and second sites, such as at least a third non-terminal Cys residue at a third site within the first protein molecule. This process can be repeated to a fourth, fifth, etc. non-terminal Cys residue. The method for site-specific protein labeling can further include providing a third protein molecule that interacts with the first protein molecule to selectively block the third non-terminal Cys residue from fluorophore binding while leaving the first and second non-terminal Cys residues unblocked by the third protein molecule. When there are four, five, etc. non-terminal Cys residues, there may also be fourth, fifth, etc. proteins molecules to interact with the first protein molecule at a corresponding one of the non-terminal Cys residues to block labeling of that particular non-terminal Cys residue.

The method for site-specific protein labeling may also include separating the third protein molecule from the first protein molecule after the third protein molecule interacts with the first protein molecule and after the second fluorophore binds to the first non-terminal Cys residue which can be followed by providing a third fluorophore that is suitable to bind to the third non-terminal Cys residue. This process is not limited to selectively labeling two or three non-terminal Cys sites and may be extended to greater numbers as desired in the particular application.

A method for site-specific modifications of protein molecules according to an embodiment of the current invention includes providing a protein molecule having at least first and second non-terminal Cys residues at respective first and second sites within the protein molecule, providing a blocking molecule that is suitable to interact with the protein molecule to selectively block the second non-terminal Cys residue to prevent modifications of the second non-terminal Cys residue while leaving the first non-terminal Cys residue unblocked, and providing a Cys-modifying molecule that is suitable to modify the first non-terminal Cys residue. The blocking molecule according to an embodiment of the invention may be a protein molecule, DNA, an aptamer or synthetic organic molecules. The Cys-modifying molecule according to an embodiment of the invention may be a fluorophore, biotin, spin label, a sugar or a non-natural amino acid analogue. The protein molecule may be a recombinant protein molecule in which at least one of the at least first and second non-terminal Cys residues is introduced or re-introduced at a selected site within the protein molecule.

The method for site-specific modifications of protein molecules according to an embodiment of the current invention may include separating the blocking molecule from the protein molecule after the blocking molecule interacts with the protein molecule to selectively block the second non-terminal Cys residue and after the Cys-modifying molecule modifies the first non-terminal Cys residue. The method for site-specific modifications of protein molecules according to an embodiment of the current invention may further include providing a second Cys-modifying molecule that is suitable to modify the second non-terminal Cys residue after separating the blocking molecule from the protein molecule. The protein molecule according to embodiments of the current invention may have at least a third non-terminal Cys residue at a third site within the protein molecule, at least a fourth non-terminal Cys residue at a fourth site within the protein molecule, etc. The method for site-specific modifications of protein molecules according to an embodiment of the current invention may further include providing a second blocking molecule that is suitable to interact with the protein molecule to selectively block the third non-terminal Cys residue to prevent modifications of the third non-terminal Cys residue while leaving the first and second non-terminal Cys residues unblocked by the second blocking molecule. In other embodiments of the current invention, a third blocking molecule may be provided to selectively block a fourth non-terminal Cys residue, etc. for the number of blocking molecules desired for the particular application. The method for site-specific modifications of protein molecules according an embodiment of the current invention may further include separating the second blocking molecule from the protein molecule after the second blocking molecule interacts with the protein molecule and after the second Cys-modifying molecule modifies the second non-terminal Cys residue. The method for site-specific modifications of protein molecules according to an embodiment of the current invention can further include providing a third Cys-modifying molecule that is suitable to modify the third non-terminal Cys residue.

A method of producing a product according to some embodiments of the current invention includes labeling a plurality of protein molecules according to the above-noted methods.

A method of producing a product according to some embodiments of the current invention includes modifying a plurality of protein molecules according to the above-noted methods.

DESCRIPTION OF THE DRAWINGS

The invention is described herein, by way of example only, with reference to the accompanying figures, in which like components are designated by like reference numerals, in which

FIGS. 2(a)-2(c) illustrate a probing protein-protein interaction via FRET and estimation of the dissociation constant of the complex between CI2 and the inactive Sbt-variant.

FIGS. 3(a)-3(d) show Thiol-accessibility assay of the engineered Cys1' and Cys40 residues in CI2. Absorbance spectra obtained with FIG. 3(a) CI2-Cys40 and FIG. 3(b) CI2-Cys1'/Cys40 in the absence (blue line) and presence (red line) of a two-fold stoichometric excess of Sbt after addition of a ten-fold stoichometric excess of A647 and incubation for 4 h at 25° C. Unreacted A647 was removed by gel filtration before absorbance spectra were taken. FIG. 3(c) shows the absorbance spectrum of A/D-labeled CI2-Cys1'/Cys40, prepared according to FIG. 1(b). FIG. 3(d) shows the fluorescence emission spectrum of the sample shown in FIG. 3(c) under native conditions (0 M GdnCl, blue line) and denaturing conditions (6 M GdnCl, red line).

FIGS. 4(a)-4(f) show probing labeling quality by alternating-laser excitation (ALEX) and fluorescence aided molecular sorting (FAMS). Sorting in ALEX-FAMS is achieved in 2-D histograms using the FRET-efficiency (E) and the ALEX-ratio (S) as independent variables. E sorts species according to FRET (inter-dye distance), S sorts on the D/A-stoichometry (fluorophore-labeling). E-S histograms for FIG. 4(a) D-only labeled CI2-Cys40, FIG. 4(b) A-only labeled CI2-Cys40, and FIGS. 4(c)-4(f) A/D-labeled CI2 Cys1'/Cys40 at various denaturant concentrations are shown.

FIGS. 5(a)-5(d) show thermodynamic analysis of chemically unmodified and fluorophore-labeled CI2-Cys1'/Cys40.

FIG. 7 illustrates another embodiment of the current invention.

DETAILED DESCRIPTION

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

According to an embodiment of the invention protein-protein interactions can be utilized to site-specifically label recombinantly expressed multi-Cys proteins. Protein-protein interactions are ubiquitous and characterized by the burial of large surface areas (average buried area~1600 Å) in a binding interface.[38-41] We rationalized that the burial of surface area upon protein-protein interactions can be exploited according to an embodiment of the current invention to physically protect engineered Cys side chains, participating in such binding interfaces, from conjugation with extrinsic fluorophores. A second Cys that is not part of the interaction interface and that remains solvent-exposed after complex formation can thus be selectively labeled in the pre-assembled complex. Labeling of the protected Cys in the interface with a complementary FRET-fluorophore can be achieved upon dissociation/denaturation of the protein assembly in the presence of high concentrations of chaotropes, followed by separation of the interacting domains via gel filtration (if the difference in size between the interacting domains is sufficiently high) or immobilized-metal-affinity-chromatography (if one of the two interacting domains is tagged with a hexa-histidine-label). The feasibility of this approach is demonstrated using the binary complex between chymotrypsin inhibitor 2 (CI2) and the serine protease subtilisin BPN' (Sbt) as an example.

EXAMPLE

I. Methods
Materials

Alexa Fluor 488 maleimide (A488 hereafter), Alexa Fluor 594 maleimide (A594 hereafter) and Alexa Fluor 647 maleimide (A647 hereafter) were purchased from Molecular Probes (Eugene, Oreg. USA). Guanidinium thiocyanate (GdnSCN) was from Sigma, Guanidinium chloride (GdnCl, sequanal grade) was from Pierce.

A plasmid for recombinant expression of a truncated 64-residue double mutant (Glu26Ala/Lys53Arg) of CI2, obtained by deletion of the first, unstructured 19 amino acids residues and replacement of Leu20 with a new starting Met was a gift from Dr. Daniel Koshland (UC Berkeley, Calif.). This truncated and mutated protein sequence has been shown to retain the complete structure and function of full-length CI2 and is referred to as wildtype (wt) hereafter.[42,43]

Figure 1:
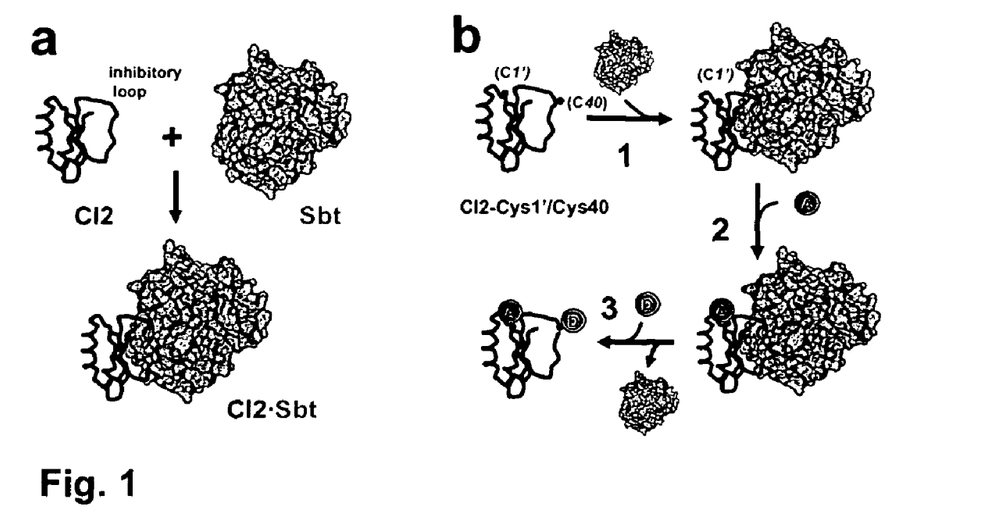
FIG. 1(a) shows X-ray structures of unliganded chymotrypsin inhibitor 2 (CI2) (magenta) and CI2 in complex with the serine protease subtilisin BPN' (Sbt) (light grey). CI2 is represented as $C^\alpha$-backbone with side chains not shown explicitely. Sbt is depicted with the solvent-accessible surface area shown explicitely.
FIG. 1(b) illustrates the concept of site-specific-labeling of interacting proteins, demonstrated with the CI2•Sbt complex shown in FIG. 1(a). The position of the engineered Cys (Cys1', Cys40) in CI2 is indicated by filled blue spheres overlaid onto the $C^\alpha$-backbone of the inhibitor.

Three additional CI2 variants are described herein. The first mutant is a single-Cys variant in which Met40 in the inhibitory loop was replaced by a Cys (dubbed CI2-Cys40 hereafter). This mutant is used as a control to proof site-specific labeling of a double-Cys variant of CI2 in the CI2•Sbt complex. The second variant carries a unique Cys engineered between the initiation methionine (Met1) and lysine at position 2. Electrospray-ionization mass spectrometry indicates that Met1 is not proteolytically removed in vivo (data not shown). In order to retain the amino-acid numbering scheme of wt-CI2, the inserted Cys was dubbed Cys1', and the corresponding CI2-variant called CI2-Cys1'. CI2-Cys1' is used to probe the affinity between CI2 and subtilisin using intermolecular FRET and to give an upper estimate of the dissociation constant for the CI2•Sbt-complex. The third variant (dubbed CI2-Cys1'/Cys40 hereafter) contains both Cys1' and Cys40 (FIG. b). The CI2-Cys1'/Cys40 variant is used for labeling with a unique D/A-FRET pair.

A plasmid for the expression of a catalytically inactive and stability-engineered variant of subtilisin BPN' (dubbed wildtype (wt) Sbt hereafter)[44] was kindly provided by Dr. Bryan (CARB, University of Maryland Biotechnology Institute, Rockville, Md). A variant of Sbt that contains a cysteine-glycine insertion after the initiation methionine of wt-Sbt (dubbed Sbt-Cys hereafter) was also constructed.

All site-directed mutagenesis experiments were performed using the Stratagene Quickchange site-directed mutagenesis kit (Stratagene, La Jolla, Calif.).

Protein Expression and Purification

The expression and purification of wt-CI2, wt-Sbt, and variants thereof, were performed as described.[42-44] Purified wt-CI2 and wt-Sbt were dialyzed against buffer B (20 mM sodium phosphate, pH 7.0, 100 mM sodium chloride) stored at 4° C. until further use. The Cys-variants were stored in buffer A (20 mM sodium phosphate, 100 mM sodium chloride, pH 7.0, 10 mM dithiotreitol (DTT)) until used in labeling experiments.

Protein Labeling

Labeling of single-Cys proteins: For the labeling of CI2-Cys1', CI2-Cys40 and Sbt-Cys, a quantity of freshly-purified protein (in buffer A) was passed through a PD10 column (Pharmacia), equilibrated in buffer B. A ten-fold excess of maleimide-fluorophore (in buffer B) was added to the solution and incubated for 4 h at 25° C. The protein solution was washed extensively on a Centricon YM3 centrifugal filter membrane (Millipore Corporation, Bedford, Mass.) to remove excess unreacted fluorophore. Singly-labeled protein solutions were stored at 4° C. in the dark until further use.

Selective labeling of double-Cys CI2 in the CI2•Sbt-complex: Two doubly-labeled CI2 variants are described in the text. In the first variant, Cys 1' is labeled with A647 (A) and Cys40 is labeled with A488 (D) (A/D-labeled CI2 hereafter). In variant 2, the dye positions are permutated and Cys 1' is labeled with A488, while Cys 40 is modified with A647 (D/A-labeled CI2 hereafter).

To prepare A/D-labeled CI2, a quantity of purified and reduced CI2-Cys1'/Cys40 (10 pM, in buffer A) was incubated with a two-fold excess of wt-Sbt (in buffer B) and incubated for 30 min at room temperature to allow complex formation. The reducing agent was removed by passing the CI2•Sbt complex through a PD10 column, equilibrated in buffer B. A ten-fold excess of A647 (in buffer B) was added to the protein solution and incubated for 4 h at 25° C. in the dark. Unreacted dye was removed by extensively washing the protein solution with buffer B on a Centricon YM-3 centrifugal filter. To release CI2-Cys1'/Cys40 (singly-labeled with A647 at Cys1') from the CI2•Sbt complex, the protein solution was mixed with a stock solution of GdnSCN (in buffer B) to give a final concentration of 6 M denaturant. After incubation for 2 h 25° C. in the dark, a ten-fold excess of A488 (in buffer B) was added to the solution and incubated for another 4 h at 25° C. in the dark. Unreacted dye was removed by extensive washing of the protein solution with buffer B by repeated concentration/dilution on a Centricon YM3-membrane. The concentrated protein solution was passed through a PD10 column, equilibrated in buffer C (20 mM sodium phosphate, pH 7.0, 40 mM NaCl) to remove denaturant. After 10 minutes (to allow denatured CI2 to refold), the eluted protein sample was injected onto a HighLoad 16/60 Superdex 75 size exclusion column (Pharmacia), equilibrated in buffer C. At the low salt concentration employed, refolding of Sbt (26 kDa) is extremely slow (rate constant of $5 \cdot 10^{-5}$ s$^{-1}$)[44] and rebinding of CI2 to Sbt during size-exclusion chromatography is negligible (data not shown). Elution of denatured Sbt occurs before the smaller A/D-labeled CI2 (~9 kDa, including dyes). Peak fractions containing A/D-labeled CI2 were pooled, buffer exchanged into buffer D (20 mM sodium phosphate, pH 6.3) and stored at 4° C. in the dark until used. D/A-labeled CI2 was prepared accordingly by changing the order of the added dyes.

Estimation of the Dissociation Constant of the CI2•Sbt-complex

A given quantity of A488-labeled CI2-Cys1' (50 nM CI2 in buffer B, 0.01% BSA (w/v)) was titrated with a stock-solution of A594-labeled Sbt and incubated for 24 h at 25° C. The protein solution was transferred into a quartz cuvette and fluorescence emission spectra were recorded between 490 - 740 nm (excitation at 470 nm). An upper limit for the dissociation constant of the binary complex was estimated by plotting the integrated acceptor fluorescence emission intensity (direct excitation of the acceptor at 470 run is negligible) between 600 - 740 nm against the Sbt-concentration.

Labeling Specificity in the CI2•Sbt Complex

A quantity of reduced CI2-Cys40 or CI2-Cys1'/CysC40 (10 μM, in buffer B) was mixed with a two-fold excess of wt-Sbt (in buffer B) and incubated for 30 min to allow complex formation. A ten-fold excess of A647 (or A488) was added and the solution was incubated for 4 h at 25° C. in the dark. Excess dye was removed by repeated concentration/dilution of the protein solution in a Centricon YM3 concentration device until the absorbance of the flow-through fraction at 647 nm (or 488 nm) was negligible. The washed protein solution was transferred to a 1.5 ml Eppendorf tube. The volume of the solution was adjusted to 1 ml and transferred to a 10 mm quartz cuvette. Absorbance spectra were recorded from 220 nm to 760 nm in a Perkin Elmer model Lambda 25 UV/V is spectrophotometer (Perkin Elmer, Boston, Mass.). The extent of Cys-labeling was judged from the sample absorbance at 647 nm (absorbance maximum of A647) or 488 nm (absorbance maximum of A488).

Thermodynamic Analysis

Stability measurements were performed by mixing CI2 with increasing amounts of chaotrope (0 - 6 M GdnCI). Denaturant concentrations were determined refractometrically[45]. The thermodynamic stability of unlabeled wt-CI2 was determined by monitoring the increase in fluorescence emission of the single tryptophan (Trp5) upon unfolding. Protein concentrations of 5 μM (in buffer D) were employed. After incubation for 4 h at 25° C., fluorescence emission spectra were recorded from 310 nm to 420 nm (excitation at 295 nm).

The stability of the D/A-labeled CI2-Cys1'/Cys40 variant (or the A/D-permutant thereof) was determined by recording acceptor fluorescence emission spectra from 650 nm to 740 nm after excitation at 488 nm (A-emission due to FRET) and 630 nm (direct excitation of A) as a function of denaturant concentration. A protein concentration of 10 nM was used.

Changes in free energy of folding ($\Delta G_{N-U}$) were estimated by a six-parameter least-squares fit, assuming a two-state unfolding model:[46]

$$S_{obs} = \frac{((S_{folded} + m_{folded}[D]) + (S_{unfolded} + m_{unfolded}[D])) \exp\{-(\Delta G_{N-U} - m_G[D]/RT)\}}{1 + \exp\{-(\Delta G_{N-U} - m_G[D]/RT)\}} \quad (1a)$$

$S_{obs}$ is either the observed integrated fluorescence emission between 310 nm and 420 nm (unlabeled CI2) or the integrated fluorescence intensity of A647 after excitation of the donor at 488 nm, normalized by the integrated fluorescence intensity of A647 after direct excitation (630 nm) at denaturant concentration [D], $S_{folded}$, $S_{unfolded}$, $m_{folded}$ and $m_{unfolded}$ represent intercepts and slopes of native and unfolded baselines, respectively, $m_G$ is a cooperativity parameter related to the change in exposure of hydrophobic surface area upon unfolding[47], R is the gas constant and T the absolute temperature. Unfolding transitions were normalized to the fraction of unfolded protein, $F_u$:[46]

$$F_U = \frac{((S_{folded} + m_{folded}[D]) - S_{obs})}{((S_{folded} + m_{folded}[D]) - (S_{unfolded} + m_{unfolded}[D]))} \quad (1b)$$

Fluorescence Aided Single Molecule Sorting (FAMS)

Single molecule measurements were performed with an inverted fluorescence microscope (Zeiss Axiovert 100, 100× 1.4 NA oil-immersion objective, 100 µm pinhole), modified to allow alternating-laser-excitation (ALEX) using a two-laser excitation source (488 nm Ar+-laser, 638 nm diode-laser). A detailed description of ALEX is given elsewhere.[48] Briefly, alternation of the two lasers with a period of 100 µs, a timescale faster than the residence time in the confocal spot (~600 µs for CI2) allows simultaneous, direct probing of both A488 (D) and A647 (A) in the diffusing CI2 molecule. ALEX allows the fluorescence-aided molecular sorting of species that differ in their emission profiles using two ratiometric expressions, the traditional FRET-efficiency E, and the stoichiometry ratio S. The FRET-efficiency E is defined as:

$$E = \frac{F_{Dexc}^{Aem}}{F_{Dexc}^{Aem} + \gamma F_{Dexc}^{Dem}} \quad (2a)$$

$F_{Dexc}^{Dem}$ is the background-corrected D-excitation-based D-emission, $F_{Dexc}^{Aem}$ is the D-excitation-based A-emission, and γ is a detection and quantum yield correction factor. The novel stoichometric ALEX-ratio S is defined as:

$$S = \frac{F_{Dexc}}{F_{Dexc} + F_{Aexc}} \quad (2b)$$

$F_{Dexc}$ is the sum of D-excitation-based emissions, $F_{Aexc}$ is the sum of A-excitation-based emissions. For a D-only molecule (e.g. single D-fluorophore or bleached A-fluorophore), $F_{Aexc}$ is negligible and S is ≈1. For an A-only molecule, both $F_{Dexc}$ and S values are around 0. The S-ratio of a D/A-labeled molecule depends on the excitation power used. If the excitation is adjusted such that $F_{Dexc} \approx F_{Aexc}$ (this study), S≈0.5.

All measurements were carried out in buffer C (20 mM sodium phosphate, pH 6.3, 100 µg/ml BSA). The concentration of the protein was 100 pM and was calculated from the absorbance of A at 647 nm. D- and A-excitation were 50 µW each. Fluorescence bursts indicating the presence of a molecule in the laser confocal spot were detected by binning the recorded photons in 500 µs bins and defining the beginning and end of a burst using a threshold (D+A photons) set such as to reject most of the background[12,49]. Only bursts containing more than 80 photons were retained for further analysis. E- and S-ratios were calculated for each burst and represented as E- or S-histograms. Denaturation studies were carried out in buffer D with GdnCl-concentrations varying from 0 M to 6 M. GdnCl from Pierce (Sequanal grade) was found to be sufficiently background-free for these single molecule experiments. Data acquisition was for 25 min, and histograms were calculated and analyzed using in-house written LabView software. Histograms were fitted to Gaussian functions using the Origin 7.5 software package (OriginLab, Northampton, Mass.) to determine apparent mean-E values of the folded and unfolded protein distributions and to calculate fractions of folded protein, as described in detail elsewhere[5].

II. Results

Protein-protein Interactions as a Tool for Site-specific Labeling of Proteins

Protein-protein interactions are among the most ubiquitous types of interactions in biological systems. Protein-protein interactions are generally characterized by large buried binding interfaces. An analysis of over 70 protein-protein complexes[39,41] showed that a typical interface buries on average about 1600±400 Å$^2$. Alanine scanning studies in 22 protein-protein complexes indicate that only fraction of those residues constituting a binding interface are actually important to binding energetics.[50] Therefore, it should be possible to introduce a Cys residue into the binding regions of protein known to be engaged in high affinity protein interactions without severely compromising its binding affinity. Upon protein-protein interaction, the engineered Cys in the interface region will become surface-inaccessible and protected from conjugation with thiol-specific fluorophores, while a second, solvent-accessible Cys that is not part of the binding interface should be susceptible to labeling.

We tested the concept of selective protection of cysteines upon protein-protein interaction using chymotrypsin inhibitor 2 (CI2) and subtilisin BPN' (Sbt) as model proteins. CI2, a small 64-residue single-domain protease inhibitor binds with high affinity (KD=3.0×10$^{-12}$ M$^-$) to catalytically active Sbt BPN', a serine protease (FIG. 1(a)).

The recognition site of the CI2 inhibitor, known as the inhibitory loop, forms a single-patch interface of standard buried surface area (1630 Å$^2$) with the active site region of Sbt.[42,43] As bound inhibitor is cleaved by active Sbt and a long-lived acyl-enzyme intermediate is formed[42], a catalytically impaired Sbt variant was used for labeling.[44] As wt-CI2 is devoid of Cys-residues, two Cys were engineered into the inhibitor sequence. The first Cys (dubbed Cys1') was inserted between the initiation methionine (Met1) and lysine 2 (Lys2) at the N-terminus. The second Cys substitutes methionine (Met) at position 40 (Cys40) in the center of the inhibitory loop (FIG. 1(b)). The side chain of Met40 is solvent-accessible in the unliganded CI2, but is completely buried in the CI2•Sbt complex. Site-directed mutagenesis data implies that Met40 is neither important for protein stability nor required for high-affinity complex formation.[51-53]

Selective labeling of the two engineered Cys in CI2 is achieved in three steps (FIG. 1(b)). First, the binary CI2•Sbt complex is assembled at micromolar concentrations (dissociation constant of the CI2•Sbt complex <<50 nM, see below) to protect Cys40 in the binding interface. Second, A647 is added to label the exposed thiol-moiety of the solvent-accessible Cys1' residue at the N-terminus. Excess unreacted dye is removed by gel filtration. Third, the complex between the singly-labeled CI2 and Sbt is denatured in the presence of high concentrations of denaturant to deprotect the buried Cys40. The now accessible Cys40 side-chain is labeled with A488 under denaturing conditions (to prevent reassociation with the protease) and CI2 is separated from the protease by size exclusion chromatography. A variant of CI2, in which the position of the dyes is permutated (D/A-labeled CI2-Cys1'/Cys40), has been prepared analogously by changing the order of the added dye (A488 added in step 2, A647 added in step 3).

Probing the Affinity of the CI2•Sbt Complex Using Intermolecular FRET

The high affinity (K$_D$=3.0×10$^{-12}$ M) of wt-CI2 for the catalytically active wt-Sbt has been attributed to the fast cleavage of the inhibitor backbone and the formation of a long-lived covalent acyl-enzyme adduct.[42] It is known that inactive Sbt exhibits lower substrate binding affinities towards peptidogenic substrates[42], but unfortunately no dissociation constants have been reported.

Figure 2:
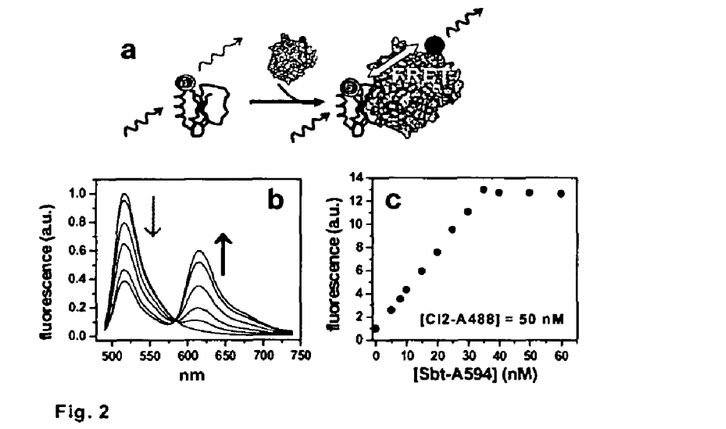
FIG. 2(a) is a schematic depiction of the intermolecular FRET-assay employed to monitor the formation of the CI2•Sbt-complex from A488 (D)-labeled CI2 and A594 (A)-labeled Sbt.
FIG. 2(b) shows fluorescence emission spectra of A488-labeled CI2 (50 nM) in the presence of increasing concentrations of A594-labeled Sbt (excitation: 470 nm). Complex formation leads to a decrease in the D-fluorescence and a simultaneous increase in A-fluorescence. Direct excitation of A is negligible at 470 nm.
FIG. 2(c) shows the change in integrated fluorescence emission of the A594-acceptor between 600 - 720 nm of the spectra shown in FIG. 2(b) upon D-specific excitation at 470 nm plotted as a function of [A594-Sbt].

In order to show that the inactive Sbt variant binds to CI2 with sufficiently high affinity to afford site-specific protection of the interface Cys40 at the protein concentrations employed for labeling (10 - 20 μM), we performed an intermolecular ensemble-FRET experiment (FIG. 2(a)). CI2-Cys1' and Sbt-Cys are labeled at the N-termini with A488 (D) and A594 (A), respectively. The N-termini are spatially separated from the interface region (thus making fluorophore-induced destabilization of the complex unlikely), but are brought in sufficiently close proximity upon complex formation to enable FRET between D and A (distance between the N-termini≈54 Å; $R_0^{(A488/A594)} \approx 60$ Å).

Excitation of A488-labeled CI2-Cys1' (protein concentration=50 nM) at 470 nm results in strong D-fluorescence (spectral range 500 - 580 nm; emission maximum at 510 nm), but minimal emission in the A594-typical spectral range between 600 and 740 nm (FIG. 2(b)). Addition of A594-labeled Sbt-Cys (A594 is not excited directly at 470 nm) leads to a decrease in A488-fluorescence and a concomitant increase in A594-fluorescence (emission maximum: 620 nm), indicating FRET between A488 and A594 and demonstrating domain-domain association at nanomolar protein concentrations (two orders of magnitude less protein than used in labeling). Addition of A594-labeled Sbt to a solution of A488-labeled CI2 containing a twenty-fold excess of unlabeled CI2 did not result in an increase in A594-fluorescence (data not shown), ruling out unspecific association between the two labeled proteins.

FIG. 2(c) depicts the integrated change in fluorescence between 600- 720 nm as a function of the concentration of labeled Sbt added (data are normalized to the fluorescence intensity in the absence of labeled Sbt). The fluorescence intensity increases linearly with [Sbt] up to concentrations of ≈40 nM, above which no further increase is observed. Such a linear dependence with a pronounced kink at protein concentrations close to the equivalence point, where both domains are present at identical concentrations, is expected if the protein concentrations employed are significantly higher than the dissociation constant of the complex and the stoichometric limit is reached.[54] The equivalence point at [Sbt] ≈40 nM is slightly lower than the theoretical value of 50 nM (assuming a 1:1 stoichometry and quantitatively labeled protein samples), but is expected for a Sbt sample with a A594-labeling efficiency of 80-85% (estimated from MALDI-TOF mass spectra, data not shown).

Labeling Specificity in the CI2•Sbt Complex

Figure 3:
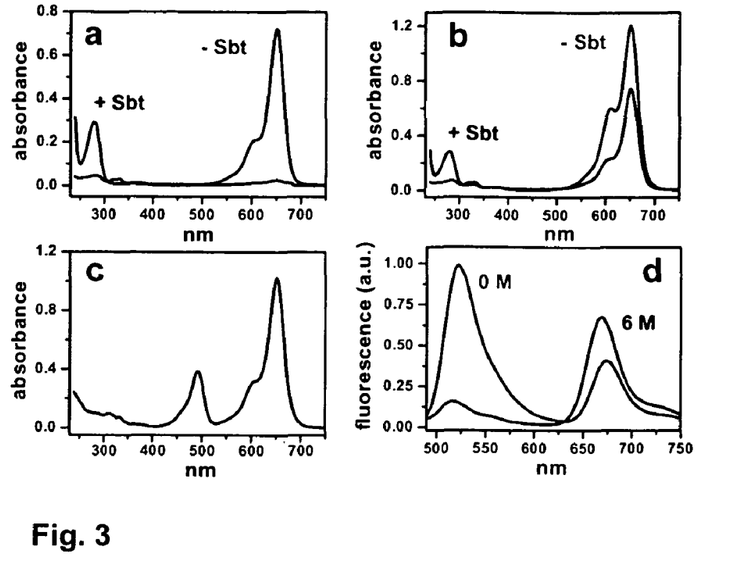

To demonstrate that Cys40 in the inhibitory loop is protected in the Sbt•CI2-Cys1'/Cys40 complex, we performed a dye-accessibility experiment. First, we incubated CI2-Cys40 with or without a two-fold stoichiometric excess of functional and affinity-purified wt-Sbt (Cys-free). A ten-fold excess of A647 was added to the solution to quantitatively label any accessible thiol-moieties. Excess dye was removed by filtration and the extent of A647-labeling estimated from absorption spectra taken with the protein solution. FIG. 3(a) shows that while the sample containing the CI2-Cys40 variant (but no Sbt) was clearly labeled by A647 (as demonstrated by the A647-typical absorption band with a maximum around 647 nm and a shoulder at 600 nm), no measurable dye absorbance was detectable when A647 was added to the preassembled Sbt•CI2-Cys40 complex. The minor peak at 280 nm observed in the Sbt•CI2-Cys40 can be attributed to the high content of tyrosines (Tyr) and tryptophans (Trp) residues in Sbt (Sbt: 3 Trp, 10 Tyr; CI2: 1 Trp, 1 Tyr). We conclude that complex formation renders the buried Cys40 inaccessible to the added fluorophore and no unspecific labeling of either CI2 or Sbt has occurred (the sample containing the Sbt•CI2-Cys40 complex shows no absorbance at 647 nm). Experiments performed with A488 gave comparable results (data not shown).

In order to show that the N-terminal Cys can be labeled in the binary complex, we repeated the experiment with the CI2-Cys1'/Cys40 variant. In the presence of a two-fold stoichometric excess of Sbt, the absorbance spectrum was essentially superimposable to the spectrum obtained with CI2-Cys40 in the absence of Sbt (FIG. 3b). We conclude that Cys1' at the N-terminus is labeled with A647, while the buried Cys40 remains protected. In the absence of Sbt, the area under the absorbance spectrum (500-760 nm) is roughly twice as high, an indication that both Cys1' and Cys40 are efficiently labeled.

FIG. 3(c) shows a representative absorbance spectrum of A/D-labeled CI2-Cys1'/Cys40, prepared according to FIG. 1(b). The presence of two absorbance bands with maxima at 647 nm (typical for A647) and 488 nm (typical for A488) is strong evidence that singly-labeled CI2-Cys1'/Cys40 can be released from the complex with Sbt and that the deprotected Cys40 can be modified by the second fluorophore added.

A fluorescence emission spectrum (excitation: 470 nm), obtained with the same sample is shown in FIG. 3(d). The emission band around 510 nm is due to D-emission. As direct excitation of A is negligible at 470 nm, the additional red-shifted emission peak must result from A-emission, due to FRET between the D and A fluorophores. Unfolding of CI2 in the presence of 6 M GdnCl leads to a pronounced increase in D-fluorescence, and a decrease in A-fluorescence, consistent with an expected increase in the D/A-distance in the polypeptide chain.

Characterization of the Labeled Products Using FAMS

To further characterize the quality of labeling, we next performed experiments at the single molecule level. ALEX is a recently developed single molecule spectroscopy that can be used for fluorescence-aided molecular sorting (FAMS) of freely-diffusing molecules.[48] In ALEX-FAMS, single molecules are detected as bursts of fluorescence photons produced as they diffuse through a focused laser excitation volume. Both D and A in a D/A-labeled sample can be excited directly at an alternation period shorter than the diffusion time of the molecule through the excitation volume, allowing the determination of FRET-efficiencies (E) outside the dynamic range of the particular FRET-pair used (E<0.2 or E>0.9), due to coincidence detection of the D and A.

Figure 4:
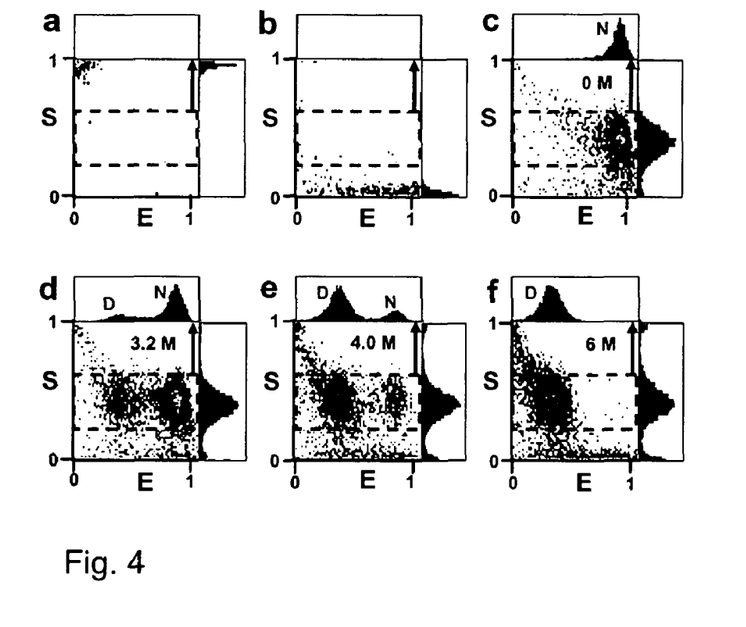

FIG. 4 depicts representative 2D S-E histograms of D-only-labeled CI2-Cys40 (panel a), A-only-labeled CI2-Cys1' (panel b) and A/D-labeled CI2-Cys1'/Cys40 (at various concentrations of denaturant; panels c-f). 1-D histograms of the stoichiometric ALEX-ratio S (shown in blue color to the right of each 2-D E-S-histogram) are obtained by projection of the entire 2-D S-E-histograms onto the vertical S-axis. Both D-only-labeled CI2-Cys40 and A-only-labeled CI2-Cys1' exhibit the expected unimodal distribution of S with mean-S values close to 1 (D-only) or 0 (A-only). The A/D-labeled CI2 Cys1'/Cys40 sample shows a single subpopulation (>95% of histogram area) with an S-value ≈0.5, which must arise from protein molecules that contain both D- and A-fluorophores. Notably, both D-only and A-only subpopulations are essentially absent in the A/D-labeled CI2 sample. It should be stressed that the lack of D-only and A-only species does not depend on the particular threshold size used (in this study, >80 photons per burst), as significantly lower values (10 photons per burst) resulted in similar S-histograms, but with larger width due to shot-noise (data not shown). This indicates that both labeling steps (step 2 and 3 in FIG. 1(b)) must have occurred essentially quantitatively, as any non-reacted Cys1' most likely would have been modified upon complex dissociation in the presence of a ten-fold stoichiometric access of A488 (step 3, FIG. 1(b)). The observation of a single A/D-labeled subpopulation is also consistent with a 1:1-labeling inferred from MALDI-TOF and ESI mass spectra (data not shown). Increasing the denaturant concentrations leads to an increase of both the D-only subpopulation, and in particular, the A-only subpopulation. As buffer/chaotrope solutions do not show any significant D-only or A-only events, the most plausible cause for the increase in the D-only and A-only subpopulation is a chaotrope-sensitized photobleaching of the D- and A-fluorophore. Further experiments are needed to clarify this point.

1-D histograms of the FRET-efficiency E for each sample are displayed at the top of each 2-D E-S histogram (histograms shown in purple). To construct these 1-D E-histograms we exploited the fluorescence aided molecular sorting capabilities of ALEX and projected only the section of the 2-D E-S-histogram onto the horizontal FRET-efficiency axis that contains A/D-labeled CI2 species (0.20<S-ratio<0.60, selected area indicated by dashed purple box). Although not relevant in this study (sample labeling was essentially quantitative), this option removes the D-only and A-only species that contaminate E-histograms obtained with partially labeled protein samples and traditional single laser excitation[5,6,55] and is thus particularly useful for the extraction of accurate mean-E values and sub-populations that significantly overlap with the D-only (E<0.2) or A-only (E>0.8) subpopulations.

Under conditions where CI2 is folded ([GdnCI] <2.5 M), a unimodal, high-FRET distribution (E ≈0.95, S ≈0.45) is observed (FIG. 4(C)). Higher denaturant concentrations lead to unfolding of CI2 and the co-existence of both high-FRET and low-FRET sub-populations (FIG. 4(d) and 4(e)). At [GdnCI] >5 M, the unfolding process is complete and only the low-FRET sub-population is visible (FIG. 4(f)).

Effect of Labeling on Protein Folding Energetics

Protein labeling with large, aromatic extrinsic fluorophores is frequently accompanied by a decrease in protein stability,[6,22] indicating a perturbation of free energy landscape of folding by the attached dye. To test the effect of fluorophore labeling on the folding thermodynamics of CI2 and to detect a possible dependence protein stability on a particular dye positioning in the polypeptide chain (A/D-labeled CI2 vs D/A-labeled CI2), protein stabilities of labeled and non-labeled CI2 was measured at ensemble and the single molecule level.

CI2 contains a single tryptophan (Trp) residue that can be used as an intrinsic reporter to study protein folding.[51] In native CI2, the single Trp is buried in the hydrophobic stability core and its fluorescence is almost complete quenched. Unfolding of CI2 in buffer solutions with increasing amounts of denaturant results in an approximately nine-fold increase in Trp-fluorescence (FIG. 5(a)). Fitting the change in integrated Trp-fluorescence emission (310 - 420 nm) to a two-state model[46] yields a folding free energy ($\Delta G_{N-U}$) of 27.4±0.5 kJ mol$^{-1}$ and an unfolding cooperativity ($m_G$-value) of 7.6±0.2 kJ mol$^{-1}$ M$^{-1}$.

Figure 5:
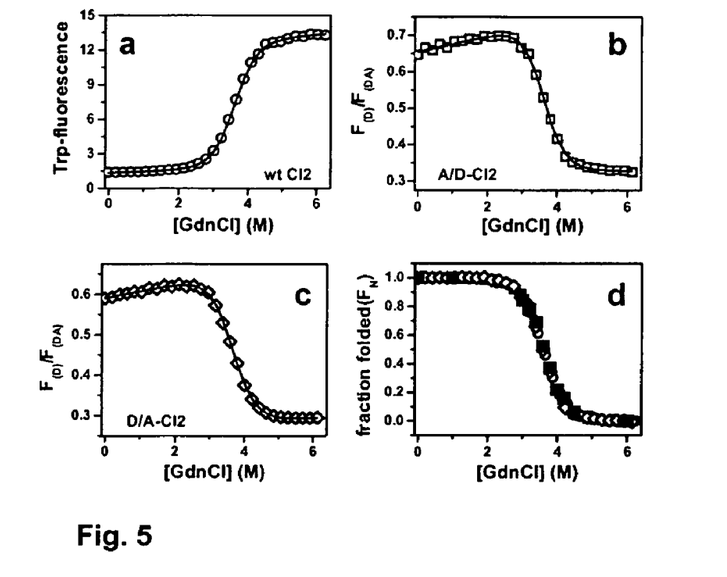
FIG. 5(a): Denaturation of unlabeled CI2-Cys1'/Cys40, followed by the change in Trp-fluorescence emission intensity.
FIGS. 5(b) and 5(c): Ensemble denaturation curve of A/D-labeled CI2-Cys1'/Cys40 FIG. 5(b) and D/A-labeled CI2-Cys1'/Cys40 FIG. 5(c). The change in the A-emission after D-excitation ($F_{DA}$), normalized to A-emission ($F_A$, excitation at 633 nm) is shown. Solid lines in FIGS. 5(a) to 5(c) represent fits of the raw data to a two-state unfolding model (equation 1a).
FIG. 5(d) is for unfolding transitions shown in FIGS. 5(a) to 5(c) after normalization to the fraction of folded protein ($F_N$) (equation 1b). Open circles: Unlabeled CI2, open squares: A/D-labeled CI2, open rhombuses: D/A-labeled CI2. Also shown are the data obtained with A/D-labeled CI2 (filled red spheres) from single molecule measurements.

To extract thermodynamic stabilities of A/D- and D/A-labeled CI2, we first monitored, on the ensemble level, the integrated change in fluorescence emission from 650 nm to 740 nm ($F_{(DA)}$) of the A647 acceptor (A), after D-specific excitation at 470 nm (FIG. 3(d)). To account for small variations in fluorescence intensity due to adsorption of the labeled protein to the quartz cuvette at the low protein concentrations employed (10 nM), we normalized $F_{(DA)}$ by the integrated fluorescence emission intensity of A after direct excitation at 630 nm ($F_{(A)}$), and used the ratio $F_{(DA)}/F^{(A)}$ as a progress coordinate for unfolding. Raw data obtained with D/A-labeled and A/D-labeled CI2-Cys1'/Cys40 are shown in FIG. 5(b) and 5(c), respectively. In both cases the $F_{(DA)}/F_{(A)}$-ratio decreases sigmoidally with increasing concentrations of denaturant, approaching a baseline level at [GdnCI] >5 M. The decrease in $F_{(DA)}/F_{(A)}$ is consistent with an increase in the inter-dye distance upon unfolding. Free energies of folding and cooperativity m-values of D/A-labeled and A/D-labeled CI2 are almost identical to those measured for the unmodified wt CI2 reference (D/A-labeled CI2: $\Delta G_{N-U}$=27.2±0.6 kJ mol$^{-1}$, $m_G$=7.5±0.2 kJ mol$^{-1}$ M$^{-1}$; A/D-labeled CI2: $\Delta G_{N-U}$=28.7±1.1 kJ mol$^{-1}$, $m_G$=8.0±0.3 kJ mol$^{-1}$ M$^{-1}$). Unfolding transitions, normalized to the fraction of folded protein (equation 1b), are superimposable within experimental error to the curve obtained with the unmodified CI2-reference (FIG. 5(d)). Also depicted in FIG. 5(d) are the values of fraction of folded protein (filled red spheres), obtained from FRET-denaturation experiments at the single molecule level by fitting the 1-D E-histograms (FIG. 4(c)-4(f); and data not shown) to Gaussian functions. The excellent agreement between the single molecule data and the data obtained from ensemble unfolding experiments suggests that single molecule experiments have the potential to accurately reproduce the ensemble folding experiment. From the available data, we conclude that labeling does not measurably perturb the folding free energy of CI2, nor does it affect the change in solvent-exposed area upon unfolding.

III. Discussion

We have introduced a novel approach to afford site-specific labeling of recombinant proteins for FRET-based single molecule studies. The new method, which we dub SLOPPI (for site-specific labeling of proteins using protein-protein - interactions) in the following, invokes protein-protein interactions to selectively protect engineered cysteines that become buried in a binding interface upon protein-protein interaction against labeling in a multi-cysteine protein context. Unlike statistical two-step labeling,[6,21,22] SLOPPI can be performed in simple batch-mode without the need for time-consuming two-step chromatography to separate singly-labeled protein from non- or doubly-labeled side-products required in conventional sequential-labeling. SLOPPI may thus be useful for rapid optimization of dye pairs, for example to optimize the FRET-efficiencies for protein folding studies (the FRET-efficiency E is most sensitive in the linear range where 0.3<E<0.8) or to minimize previously reported dye-induced destabilization of the labeled protein. SLOPPI may also be helpful in those cases where sequential labeling does not work, for example when neutral or zwitterionic dyes (e.g. TMR, Cy3B) are employed and the singly-labeled protein cannot be easily separated chromatographically from unlabeled or doubly-labeled side products.

Further Embodiments

The suitability of SLOPPI as a tool for site-specific labeling of proteins was demonstrated for the binary CI2•Sbt complex as a model system. The same concept can be immediately applied to label several other proteins that serve as interesting model systems for protein folding studies, and that participate in high affinity binary or multi-subunit complexes for which high-resolution structural information is available.[56-59] In addition, rapid progress in structural biology and ongoing large scale structural proteomics initiatives will continue to output large numbers of structures of protein complexes, some of which might be suitable for labeling by our new methodology.

Figure 6:
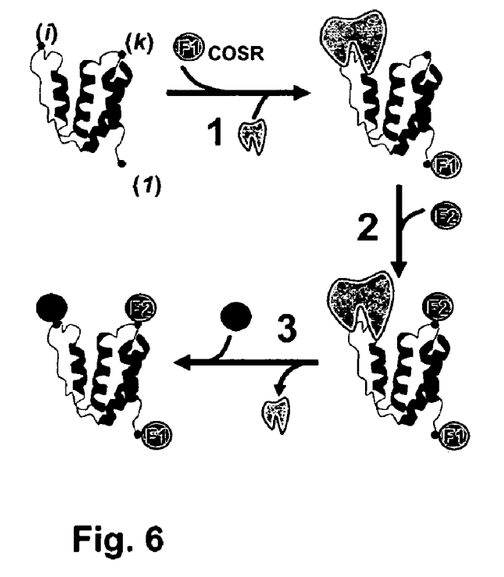
FIG. 6 shows combining selective labeling of interacting proteins and specific labeling of N-terminal Cys to afford site-specific three-color labeling of a hypothetical recombinant protein with Cys at the N-terminus, and internal positions i and k.

Because SLOPPI does not necessarily require N-terminal cysteines, it is compatible with and complementary to existing chemistries specific for N-terminal labeling.[28,30] FIG. 6 depicts how SLOPPI and specific N-terminal labeling could be combined to achieve three-color labeling of recombinantly expressed proteins for single molecule spFRET protein folding studies. A hypothetical, recombinantly expressed triple-Cys protein (depicted as a four-helix bundle (red)) with Cys at the N-terminus and at internal positions i and k along the chain (indicated by filled blue spheres) is first specifically modified at the N-terminal Cys with a thioester (COSR)-modified fluorophore[28] F1 (green circle), followed by addition of an interacting protein to render Cys i solvent-inaccessible in a binding interface (step 1). The unlabeled Cys k is then conjugated with a second commercial maleimide-functionalized fluorophore D2 (orange circle) (step 2). In the final step, the protecting protein masking Cys i is then removed by denaturation of the binary complex in high concentrations of chaotropes, followed by removal of the interacting protein via immobilized-metal-affinity-chromatography or by gel filtration. The unmasked Cys i in the doubly-labeled hypothetical is then reacted with a third commercial maleimide-functionalized fluorophore D3 (red circle) yielding the site-specific, triply-labeled protein of interest.

By using recombinant single-chain fragments (scFv) or Fab-fragments of antibodies as interacting domains and Cys-protecting tools, we envision that SLOPPI can provide a general method for site-specific protein labeling according to an embodiment of this invention. The affinity of antibody fragments directed against protein antigens is typically in the nanomolar range,[41,60,61] high enough to afford essentially irreversible binding at the micromolar protein concentrations typically employed in labeling experiments. The buried interfaces in these antibody-antigen complexes range from 1250 $Å^2$ to 2320 $Å^2$,[41,62,63] providing enough flexibility in the positioning of unique interfacial cysteines. Advanced mass spectrometric methods in combination with hydrogen-deuterium exchange[64-67] and thiol-accessibily assays similar to those described in the text can be utilized to map binding interfaces in these antibody-antigen complexes, allowing the engineering of Cys into the binding surface even if no high-resolution structural data are available.

Moreover, directed evolution of antibodies against the protein of interest,[68] together with epitope mapping, could produce several different monoclonal antibodies against different epitopes of the same target. Cys residues could be engineered into each of the epitope interfaces. Such an approach could, in principle, afford the labeling of n engineered Cys in a single chain. In the first labeling step, n–1 monoclonal antibodies will protect n–1 Cys, and only the single exposed Cys will be labeled. After denaturation and separation, n–2 monoclonal antibodies will be used to protect the remaining Cys except for the second one to be labeled. After n–1 similar steps, a single chain could be site-specifically labeled with n fluorophores.

In addition to site-specific fluorophore labeling of proteins for ensemble and single molecule FRET studies, SLOPPI in conjunction with established chemistry for modification of N-terminal proteins, enzymatic labeling of transglutaminase substrate recognition tags, or labeling of hexa-histidine tags, will also greatly facilitate three color-labeling of proteins. By generalizing the SLOPPI concept to recombinant antibodies against specific epitopes of the target protein, n site-specific modifications will be possible with n–1 available antibodies.

SLOPPI can also be useful for the selective immobilization of proteins on solid support for single molecule FRET experiments using confocal or evanescent wave excitation. The selective immobilization afforded by SLOPPI makes this technique also interesting for protein-protein interaction studies at the ensemble and single molecule level.

In addition to fluorophore labeling, SLOPPI can be used to site-specifically modify proteins with sugar moieties, spin-labels and non-natural aminoacid analogues (e.g. cross linkers) to probe structure and function in vitro.

The embodiments illustrated and discussed in this specification are intended only to teach those skilled in the art the best way known to the inventors at the time of filing to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

REFERENCES (1) Onuchic, J. N.; Luthey-Schulten, Z.; Wolynes, P. G. *Ann. Rev. Phys. Chem.* 1997, 48, 545-600.

(2) Dill, K. A.; Chan, H. S. *Nat. Struct. Biol.* 1997, 4, 10-19.

(3) Shea, J. E.; Brooks 3rd, C. L. *Ann. Rev. Phys. Chem.* 2001, 52, 499-535.

(4) Talaga, D. S.; Lau, W. L.; Roder, H.; Tang, J.; Jia, Y.; DeGrado, W. F.; Hochstrasser, R. M. *Proc. Natl. Acad. Sci USA* 2000, 97, 13021-13026.

(5) Deniz, A. A.; Laurence, T. A.; Beligere, G. S.; Dahan, M.; Martin, A. B.; Chemla, D. S.; Dawson, P. E.; Schultz, P. G.; Weiss, S. *Proc. Natl. Acad. Sci USA* 2000, 97, 5197-5184.

(6) Schuler, B.; Lipman, E. A.; Eaton, W. A. *Nature* 2002, 419, 743-747.

(7) Rhoades, E.; Gussakovsky, E.; Haran, G. *Proc. Natl. Acad. Sci USA* 2003, 100, 3197-3202.

(8) Rhoades, E.; Cohen, M.; Schuler, B.; Haran, G. *J Am. Chem. Soc.* 2004.

(9) Lipman, E. A.; Schuler, B.; Bakajin, O.; Eaton, W. A. *Science* 2003, 301, 1233-1235.

(10) Weiss, S. *Nat. Struct. Biol.* 2000, 7, 724-729.

(11) Selvin, P. R. *Nat. Struct. Biol.* 2000, 7, 730-734.

(12) Deniz, A. A.; Laurence, T. A.; Dahan, M.; Chemla, D. S.; Schultz, P. G.; Weiss, S. *Annu. Rev. Phys. Chem.* 2001, 52, 233-253.

(13) Ha, T. *Methods* 2001, 25, 78-86.

(14) Ha, T. *Biochemistry* 2004, 43, 4055-4063.

(15) Clegg, R. M. *Methods Enzymol.* 1992, 211, 353-388.

(16) Stryer, L.; Haugland, R. P. *Proc. Natl. Acad. Sci. USA* 1967, 58, 719-726.

(17) Jia, Y.; Talaga, D. S.; Lau, W. L.; Lu, H. S. M.; DeGrado, W. F.; Hochstrasser, R. M. *Chem. Phys.* 1999, 247, 69-83.

(18) Hohng, S.; Joo, C.; Ha, T. *Biophys. J* 2004, 87, 1328-1337.

(19) Liu, J.; Lu, Y. *J Am. Chem. Soc.* 2002,124, 15208-15216.

(20) Watrob, H. M.; Pan, C.; Barkley, M. D. *J Am. Chem. Soc.* 2003, 125, 7336-7343.

(21) Sinev, M.; Landsmann, P.; Sineva, E.; Ittah, V.; Haas, E. *Bioconjugate Chem.* 2000, 11, 352-362.

(22) Ratner, V.; Kahana, E.; Eichler, M.; Haas, E. *Bioconjugate Chem.* 2002, 13, 1163-1170.

(23) Moerner, W. E.; Orrit, M. *Science* 1999, 283, 1670-1676.

(24) Brasselet, S.; Moerner, W. E. *Single Molecules* 2000, 1, 17-23.

(25) Dawson, P. E.; Muir, T. W.; Clark-Lewis, I.; Kent, S. B. *Science* 1994, 266, 776-779.

(26) Muir, T. W.; Sondhi, D.; Cole, P. A. *Proc. Natl. Acad. Sci. USA* 1998, 95, 6705-6710.

(27) Tolbert, T. J.; Wong, C. H. *Angew. Chem. Int. Ed.* 2002, 41, 2171-2174.

(28) Schuler, B.; Pannell, L. K. *Bioconjugate Chem.* 2002, 13, 1039-1043.

(29) Geoghegan, K. F.; Stroh, J. G. *Bioconjugate Chem.* 1992, 3, 138-146.

(30) Shao, J.; Tam, J. P. *J. Am. Chem. Soc.* 1995, 117, 3893-3898.

(31) Zhang, L.; Tam, J. P. *Anal. Biochem.* 1996, 233, 87-93.

(32) Guillaumie, F.; Thomas, 0. R. T.; Jensen, K. J. *Bioconjugate Chem.* 2002, 13, 285-294.

(33) Chelius, D.; Shaler, T. A. *Bioconjugate Chem.* 2003, 14, 205-211.

(34) Chin, J. W.; Santoro, S. W.; Martin, A. B.; King, D. S.; Wang, L.; Schultz, P. G. *J Am. Chem. Soc.* 2002, 124, 9026-9027.

(35) Deiters, A.; Cropp, T. A.; Mukherji, M.; Chin, J. W.; Anderson, J. C.; Schultz, P. G. *J Am. Chem. Soc.* 2003, 125, 11782-11783.

(36) Wang, L.; Zhang, Z.; Brock, A.; Schultz, P. G. *Proc. Natl. Acad. Sci USA* 2002, 100, 56-61.

(37) Zhang, Z.; Smith, B. A. C.; Wang, L.; Brock, A.; Cho, C.; Schultz, P. G. *Biochemistry* 2003.

(38) Janin, J. *Proteins* 1997, 28, 153-161.

(39) Lo Conte, L.; Chothia, C.; Janin, J. *J Mol. Biol.* 1999, 285, 2177-2198.

(40) Jones, S.; Marin, A.; Thornton, J. M. *Protein Eng.* 2000, 13, 77-82.

(41) Chakrabarti, P.; Janin, J. *Proteins* 2002, 47, 334-343.

(42) Radisky, E. S.; Koshland Jr., D. E. *Proc. Natl. Acad. Sci USA* 2002, 99, 10316-10321.

(43) Radisky, E. S.; Koshland Jr., D. E. *Biochemistry* 2003, 42, 6484-6492.

(44) Bryan, P.; Wang, l.; Hoskins, J.; Ruvinov, S.; Strausberg, S.; Alexander, P.; Almog, O.; Gilliland, G.; Gallagher, T. *Biochemistry* 1995, 34, 10310-10318.

(45) Pace, C. N. *Methods Enzymol.* 1986,131, 266-280.

(46) Santoro, M. M.; Bolen, D. W. *Biochemistry* 1988, 27, 8063-8068.

(47) Myers, J. K.; Pace, C. N.; Scholtz, J. M. *Protein Sci.* 1995, 4, 2138-2148.

(48) Kapanidis, A. N.; Lee, N. K.; Laurence, T. A.; Doose, S.; Margeat, E.; Weiss, S. *Proc. Natl. Acad. Sci USA* 2004, 101, 8936-8941.

(49) Dahan, M.; Deniz, A. A.; Ha, T.; Chemla, D. S.; Schultz, P. G.; Weiss, S. *Chem. Phys.* 1999, 247, 85-106.

(50) Bogan, A. A.; Thorn, K. S. *J Mol. BioL* 1998, 280, 1-9.

(51) Jackson, S. E.; Fersht, A. R. *Biochemistry* 1991, 30, 10428-10435.

(52) Jackson, S. E.; Fersht, A. R. *Biochemistry* 1994, 33, 13880-13887.

(53) Radisky, E. S.; Kwan, G.; Lu, K.; Koshland Jr., D. E. *Biochemistry* 2004, 43, 13648-13656.

(54) Eflink, M. *Methods Enzymol.* 1997, 278, 221-257.

(55) Deniz, A. A.; Dahan, M.; Grunwell, J. R.; Ha, T.; Faulhaber, A. E.; Chemla, D. S.; Weiss, S.; Schultz, P. G. *Proc. NatL. Acad. Sci. USA* 1999, 96, 3670-3675.

(56) Buckle, A. M.; Schreiber, G.; Fersht, A. R. *Biochemistry* 1994, 33, 8878-8889.

(57) Welch, M.; Chinardet, N.; Mourey, L.; Birck, C.; Samama, J. P. *Nat. Struct. Biol.* 1998, 5, 25-29.

(58) Lim, D.; Park, H. U.; De Castro, L.; Kang, S. G.; Lee, H. S.; Jensen, S.; Lee, K. L.; Strynadka, N. C. J. *Nat. Struct. Biol.* 2001, 8, 848-852.

(59) Fieulaine, S.; Morera, S.; Poncet, S.; Mijakovic, I.; Galinier, A.; Janin, J.; Deutscher, J.; Nessler, S. *Proc. Natl. Acad. Sci USA* 2002, 99, 13437-13441.

(60) Kelley, R. F.; O' Connell, M. P. *Biochemistry* 1993, 32, 6828-6835.

(61) Hawkins, R. E.; Russell, S. J.; Baier, M.; Winter, G. *J MoL Biol.* 1993, 234, 958-964.

(62) Li, H.; Dunn, J. J.; Luft, B. J.; Lawson, C. L. *Proc. NatL. Acad. Sci USA* 1997, 94, 3584-3589.

(63) Ding, W.; Huang, X.; Yang, X.; Dunn, J. J.; Luft, B. J.; Koide, S.; Lawson, C. L. *J Mol. Biol.* 2000, 302, 1153-1164.

(64) Mandell, J. G.; Falick, A. M.; Komives, E. A. *Proc. NatL. Acad. Sci USA* 1998, 95, 14705-14710.

(65) Hughes, C. A.; Mandell, J. G.; Anand, G. S.; Stock, A. M.; Komives, E. A. *J Mol. Biol.* 2001, 307, 967-976.

(66) Anand, G. S.; Law, D.; Mandell, J. G.; Snead, A. S.; Tsigelny, I.; Taylor, S. S.; Ten Eyck, L. F.; Komives, E. A. *Proc. Natl. Acad. Sci. USA* 2003, 100, 13264-13269.

(67) Chu, F.; Shan, S.; Moustakas, D. T.; Alber, F.; Egea, P. F.; Stroud, R. M.; Walter, P.; Burlingame, A. A. *Proc. Natl. Acad. Sci USA* 2004, 101, 16454-16459.

(68) Feldhaus, M. J.; Siegel, R. W.; Opresko, L. K.; Coleman, J. R.; Feldhaus, J. M.; Yeung, Y. A.; Cochran, J. R.; Heinzelman, P.; Colby, D.; Swers, J.; Graff, C.; Wiley, H. S.; Wittrup, K. D. *Nat. Biotechnol.* 2003, 21, 163-170.

We claim:

1. A method for site-specific protein labeling, comprising contacting:
   a first protein molecule having no more than two Cys residues—a first and a second Cys residues at respective first and second sites within the first protein molecule, wherein the first Cys residue is accessible to interact with a fluorophore, and the second Cys residue is accessible to interact with a fluorophore or with a second protein molecule;
   a second protein, which is a blocking molecule, that is suitable to interact with the first protein molecule to selectively block the second Cys residue from fluorophore binding while leaving the first Cys residue unblocked; and
   a fluorophore that is suitable to bind to the first Cys residue, under conditions such that the first protein molecule and the second protein molecule bind with sufficiently high affinity to afford site-specific protection of the second Cys residue at the binding interface of the first protein molecule and the second protein molecule at a micromolar protein concentration, thereby labeling the first protein molecule specifically at the first Cys residue.

2. The method for site-specific protein labeling according to claim 1, wherein the first protein molecule is a recombinant protein molecule in which at least one of the first and second Cys residues has been introduced recombinantly at a selected site within the first protein molecule.

3. The method for site-specific protein labeling according to claim 1, further comprising separating the second protein molecule from the first protein molecule after the second protein molecule interacts with the first protein molecule to selectively block the second Cys residue and after the fluorophore binds to the first Cys residue.

4. The method for site-specific protein labeling according to claim 3, further comprising contacting the first protein molecule from which the second protein molecule has been removed with a second fluorophore that is suitable to bind to the second Cys residue, under conditions such that the first protein molecule is labeled specifically at the second Cys residue, thereby labeling the first protein molecule specifically at the second Cys residue.

5. The method for site-specific protein labeling according to claim 4, wherein the first fluorophore is a donor fluorophore and the second fluorophore is an acceptor fluorophore suitable to provide a donor-acceptor pair for fluorescence resonance energy transfer measurements, or wherein the first fluorophore is an acceptor fluorophore and the second fluorophore is a donor fluorophore suitable to provide a donor-acceptor pair for fluorescence resonance energy transfer measurements.

6. A method for site-specific modification of protein molecules, comprising contacting:
  a protein molecule having no more than two Cys residues—a first and a second Cys residues at respective first and second sites within the protein molecule, wherein the first Cys residue is accessible to interact with a Cys-modifying molecule, and the second Cys residue is accessible to interact with a Cys-modifying molecule or with a blocking molecule;
  a blocking molecule that is suitable to interact with the protein molecule to selectively block the second Cys residue to prevent modification of the second Cys residue while leaving the first Cys residue unblocked; and
  a Cys-modifying molecule that is suitable to modify the first Cys residue,
  under conditions such that the protein molecule and the blocking molecule bind with sufficiently high affinity to afford site-specific protection of the second Cys residue at the binding interface of the first protein molecule and the blocking molecule at a micromolar concentration, thereby modifying the first protein molecule specifically at the first Cys residue.

7. The method for site-specific modification of protein molecules according to claim 6, wherein the blocking molecule is selected from the group of molecules consisting of proteins, DNA, aptamers and synthetic organic molecules.

8. The method for site-specific modification of protein molecules according to claim 6, wherein the Cys-modifying molecule is selected from any organic or inorganic molecule suitable to provide covalent modification.

9. The method for site-specific modification of protein molecules according to claim 6, wherein the protein molecule is a recombinant protein molecule in which at least one of the first and second Cys residues has been introduced recombinantly at a selected site within the protein molecule.

10. The method for site-specific modification of protein molecules according to claim 6, further comprising separating the blocking molecule from the protein molecule after the blocking molecule interacts with the protein molecule to selectively block the second Cys residue and after the Cys-modifying molecule modifies the first Cys residue.

11. The method for site-specific modification of protein molecules according to claim 10, further comprising contacting the first protein molecule from which the blocking molecule has been removed with a second Cys-modifying molecule that is suitable to modify the second Cys residue, under conditions such that the first protein molecule is modified specifically at the second Cys residue, thereby modifying the protein molecule specifically at the second Cys residue.

12. The method according to claim 1, wherein the first and second Cys residues are non-terminal residues.

13. The method according to claim 6, wherein the first and second Cys residues are non-terminal residues.

14. The method according to claim 1, wherein the Kd of the binding of the first protein to the second protein is about $10^{-8}$ M to $10^{-12}$ M.

15. The method according to claim 6, wherein the Kd of the binding of the first protein to the blocking molecule is about $10^{-8}$ M to $10^{-12}$ M.

16. The method according to claim 6, wherein the blocking molecule is a second protein.

17. The method according to claim 6, wherein the blocking molecule is an antibody, single chain antibody (scFv) or Fab fragment of an antibody.

18. The method according to claim 1, wherein sufficient structural information is known for the first protein molecule to indicate that the first Cys residue is accessible to interact with a fluorophore, and/or the interface of the complex of the first protein and the second protein has been mapped.

19. The method according to claim 1, wherein the three dimensional structure is known for the first protein.

20. The method according to claim 6, wherein sufficient structural information is known for the protein molecule to indicate that the first Cys residue is accessible to interact with a fluorophore, and/or the interface of the complex of the protein molecule and the blocking molecule has been mapped.

21. The method according to claim 6, wherein the three dimensional structure is known for the first protein.

* * * * *